United States Patent
Harris et al.

(10) Patent No.: US 7,771,777 B2
(45) Date of Patent: Aug. 10, 2010

(54) APPARATUS AND METHOD FOR INSPECTING GOLF BALLS USING INFRARED RADIATION

(75) Inventors: Kevin M. Harris, New Bedford, MA (US); William Brum, Raynham, MA (US); Brian P. St. Aubin, South Dartmouth, MA (US); Thomas L. Mydlack, Rochester, MA (US); Paul A. Furze, Tiverton, RI (US)

(73) Assignee: Acushnet Company, Fairhaven, MA (US)

( * ) Notice: Subject to any disclaimer, the term of this patent is extended or adjusted under 35 U.S.C. 154(b) by 1216 days.

(21) Appl. No.: 10/867,495

(22) Filed: Jun. 14, 2004

(65) Prior Publication Data

US 2005/0276907 A1   Dec. 15, 2005

(51) Int. Cl.
    B05D 1/02      (2006.01)
(52) U.S. Cl. .................. 427/10; 427/421.1; 427/9
(58) Field of Classification Search ............... 427/8–10, 427/457, 595
    See application file for complete search history.

(56) References Cited

U.S. PATENT DOCUMENTS

| | | | |
|---|---|---|---|
| 4,641,972 A | 2/1987 | Halioua et al. | 356/376 |
| 5,130,173 A * | 7/1992 | Barten et al. | 427/314 |
| 5,461,109 A * | 10/1995 | Blair et al. | 524/839 |
| 5,777,244 A | 7/1998 | Kumagai et al. | |
| 5,938,545 A | 8/1999 | Cooper et al. | 473/407 |
| 6,271,520 B1 * | 8/2001 | Tao et al. | 250/330 |
| 6,462,303 B1 | 10/2002 | Brown | 219/121.69 |
| 6,462,812 B1 | 10/2002 | Heene et al. | 356/237.1 |
| 6,630,998 B1 * | 10/2003 | Welchman et al. | 356/394 |
| 6,960,098 B1 | 11/2005 | Tseng | 382/110 |
| 7,551,766 B2 * | 6/2009 | Harris et al. | 382/141 |
| 2001/0012389 A1 | 8/2001 | Welchman et al. | 382/141 |
| 2001/0031672 A1 * | 10/2001 | Cao et al. | 473/378 |
| 2004/0022948 A1 | 2/2004 | Brown et al. | 427/314 |
| 2004/0115361 A1 * | 6/2004 | Aegerter et al. | 427/430.1 |

FOREIGN PATENT DOCUMENTS

WO    WO 0009271 A1 *   2/2000

OTHER PUBLICATIONS

Ruddock, Wayne, "Infrared Thermography vs The Visible", www.infraredthermography.com/irvsvis.htm, Dec. 15, 2001, pp. 1-6.*

Birnie et al. Infrared observation of evaporative cooling during spin-coating processes, Optical Engineering, Jun. 1995, vol. 34, No. 6. pp. 1782-1787.*

(Continued)

*Primary Examiner*—David Turocy
(74) *Attorney, Agent, or Firm*—Daniel W. Sullivan

(57) ABSTRACT

A method for inspecting golf balls is disclosed. The method comprises the steps of providing at least one sensor capable of obtaining images of the infrared radiation emitted from the ball, obtaining at least one image of the ball using the sensor after paint or a coating has been applied to the surface of the ball, and determining whether the liquid was applied evenly on the surface of the ball. Preferably, the image is obtained during the transient period when the solvent in the paint or coating is evaporating. A number of numerical analysis can be used to determine the evenness of the paint or coating.

13 Claims, 1 Drawing Sheet

OTHER PUBLICATIONS

Agema Thermovision® 570, Advanced Test Equipment Rentals.

D Sight, Solutions for Advanced Manufacturing (SAM), Diffracto Ltd.

J.C. Martínez-Antón, H. Caníbal, J.A. Quiroga, E. Bernabeu, M. Álvaro Labajo, and V. Cortés Testillano, Enhancement of Surface Inspection by Moiré Interferometry Using Flexible Reference Gratings, Optics Express, Jun. 4, 2001, vol. 8, No. 12, pp. 649-654.

Maria E. Nadal and E. Amber Thompson, New Primary Standard for Specular Gloss Measurements, Journal of Coatings Technology, Dec. 2000, vol. 72, No. 911, pp. 61-66.

Maria E. Nadal and E. Amber Thompson, NIST Reference Goniophotometer for Specular Gloss Measurements, Journal of Coatings Technology, Jun. 2001, vol. 73, No. 917, pp. 73-80.

Moire Fringe Contouring, University of Glasgow, 2001.

Nikon Thermal Vision Laird-S270: Ultra-Compact Infrared (IR) CCD Camera Provides Advanced Features and Superb Image Quality, Nikon News.

R. Pezzoni, Laser-Shearography for Nondestructive Testing of Large Area Composite Helicopter Structures.

Tom Thompson, Charge-Coupled Device, Computer World.

Wayne Ruddock, Infrared Thermography vs The Visible, InfraredThermography.com.

Yoseph Bar-Cohen, Emerging NDE Technologies and Challenges at the beginning of the $3^{rd}$ Millennium—Part I, Part II, Jet Propulsion Laboratory, NDT.net, Jan. 2000, vol. 5, No. 1.

* cited by examiner

APPARATUS AND METHOD FOR INSPECTING GOLF BALLS USING INFRARED RADIATION

FIELD OF THE INVENTION

This invention generally relates to inspecting golf balls and more specifically to inspecting golf balls using infrared detector systems.

BACKGROUND OF THE INVENTION

The manufacture of golf balls typically involves a series of sequential processes performed at different processing stations, typically spatially separated one from another. Golf balls typically have at least a core and a dimpled cover formed over the core. The outer cover of the golf ball is formed with various materials that may be urethane elastomers, balata, ionomers or any other appropriate materials. The cover surfaces are formed with dimples of various numbers, sizes and patterns, which improve flight distance, control and stability. The golf ball cover generally contains a white or other colored concentrate, or is painted. The outer surface of the ball covers usually have the manufacturers indicia disposed thereon as well as an application of a paint or clear coat for the purposes not only of good appearance but also of improving fight distance and protecting of the indicia imprinted thereon.

Freshly coated golf balls are transported from a clear coat spray paint booth to a separate drying station at a remote location. Additional printing, such as a logo, may be applied over the cured clear coat.

Each process must be carefully monitored for quality assurance purposes. Inspections based on predetermined control criteria are performed to achieve a desired production quality. The manufacturer can manually inspect the entire lot if a given number of defective balls are found therein. Moreover, if a major defect, such as a gross cosmetic defect or a defect affecting performance or durability, is found, the manufacturer may choose to shut down the entire system.

Since automated production is faster, each of the above processes can be performed at a separate automated processing station functioning at optimal efficiency and speed, so that the overall production rate is maintained at the desired high level. For instance, pad-printing apparatus preferably includes an array of print-pads arranged to apply a production print sequentially on various locations on the surface of the golf ball, with the golf ball being indexed before being passed to the next print-pad. Also, the clear coating process preferably is performed by an automated spray painting technique utilizing a spray paint booth with one or more spray paint guns. A quick drying clear coat paint having a catalyzing agent may be used to reduce the usual clear coat drying time of about ten hours to about one hour or less.

On the other hand, automation of the manufacturing process can cause various manufacturing defects. For example, automated pad-printing equipment may leave smudges from excess ink carried by the printing pad. Vibration or improper set-up, such as improper positioning or accidental switching of the paint supply hoses cutting off paint supply to the spray guns, causes defective coating on golf balls. Moreover, the clear coat paint may periodically clog the spray booth filter, interfering with proper spraying of paint.

While clear coat spray painting operation utilizing catalyzation can significantly reduce the curing time, catalyzation can also occur in the spray booth, resulting in a thick brittle coating on the spray booth filter and increasing the probability of spray paint malfunctions. Clogging of spray guns and gelling of the clear coat during application result in inadequate clear coating of the golf ball. Moreover, transferring the freshly coated golf ball to the curing station before inspection does not alert the operator to attend to unacceptable spray painting apparatus conditions until the end of the curing process. Thus, to maintain high production rates, it is necessary to identify the defective products early on in the treatment process.

Given the quality control necessary to meet production standards and the high production rates of golf ball manufacturing plants, actions to correct a malfunction in the automated processing equipment should be taken as soon as possible. Accordingly, there is a need for speedy and efficient inspection of golf balls so that any manufacturing problem may be corrected early to reduce further production of defective balls.

A variety of automated inspection systems and methods are used in quality control of automated processing stations, such as for coating, finishing, or otherwise affecting the surface appearance of products. Most of the known automated inspection systems employ vision cameras to capture an image of the products. The products to be inspected are typically illuminated to allow the cameras to see the entire products, e.g., dimpled golf balls are illuminated to prevent shadows from forming in the dimples. For example, U.S. Pat. No. 6,630,998 discloses light-emitting diodes mounted over the golf balls to be inspected to provide constant and even light sources. U.S. Publ. app. No. 2001/0012389 discloses another golf ball inspection system using a custom lighting system. U.S. Pat. No. 5,777,244 discloses an elaborate system to illuminate golf balls. U.S. Pat. No. 6,462,812 discloses an inspection utilizing a plurality of charge-coupled device (CCD) cameras to inspect indicia on golf balls. CCD is an integrated circuit that converts light to electrical signals. Each CCD typically represents one pixel. A digital camera using CCD can comprise millions of pixels. U.S. Pat. No. 5,960,098 discloses a vision system for inspecting fruits. This system also utilizes CCD cameras, albeit with an infrared lens, to capture the images of fruits.

At least one vision inspection system employs infrared cameras for inspection. U.S. Pat. No. 6,271,520 discloses a system for inspecting fruits. This system uses a first camera in the near IR range and a second camera in the mid IR range to capture images of the products to be inspected. The background information is removed and the two images are subtracted leaving the defects. Another drawback of this system is that at least a portion of the exterior surface of the products to be inspected must be raised about 5° C. to 15° C. higher.

However, there remains a need in the art for an infrared vision system that overcomes the drawbacks of the prior art.

SUMMARY OF THE INVENTION

Hence, the invention is directed to a method for inspecting an object comprising the steps of (i) providing at least one sensor capable of obtaining images of the object in the non-visible electromagnetic radiation range, (ii) obtaining at least one image of the object using said sensor after a liquid has been applied to the surface of the object; and (iii) determining whether the liquid was applied evenly on the surface of the object. Preferably, the sensor in step (i) is capable of obtaining images in the infrared electromagnetic radiation range. The infrared electromagnetic range comprises wavelengths from about 0.75 to about 1000 micrometers, and is divided in the near infrared (0.75 to 2 micrometers), middle infrared (2 to 6 micrometers), far infrared (6 to 14 micrometers) and extreme infrared (14 to 1000 micrometers).

The image in step (ii) can be obtained in an environment substantially free of visible light or in an illuminated environment. Preferably, the image is taken during the transient period from the time when the liquid is first applied to the object to the time when object obtains thermal equilibrium. The liquid can be paint or coating or any solvent-based liquid.

The image of step (ii) comprises an array of pixels, and each pixel is represented by a numerical value indicative of a color or brightness of each pixel. In one embodiment, if the sum of the numerical values of the pixel is different from a total threshold value by more (or less) than a predetermined amount then the liquid was applied unevenly. The total threshold value can be ascertained from a calibrated object, wherein said calibrated object has the liquid evenly applied thereon. In another embodiment, the numerical value of each pixel is compared to an individual threshold value, and if a predetermined number of pixels differs from this threshold value then the liquid was unevenly applied. The individual threshold value can be ascertained from a calibrated object, wherein said calibrated object has the liquid evenly applied thereon. The individual threshold can be an average value (mean or median) of the numerical values of all the pixels.

The inspected object preferably comprises dimpled golf balls.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

Figure 1:
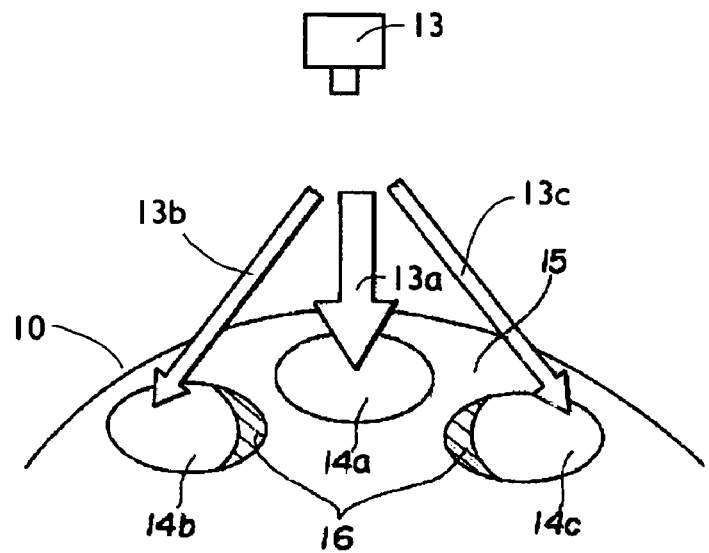
FIG. 1 is a front view of a portion of a golf ball showing an exemplary painting defect on the dimples.

As shown in FIG. 1, golf ball 10 comprises a plurality of dimples 14a, 14b, 14c et cetera defined on land surface 15. As discussed above, the spray is deposited directly on the surface of the ball. Depending on the relative location between the spray nozzle and the dimples, the spray can completely cover the dimple as illustrated schematically by arrow 13a and dimple 14a when the spray nozzle is located directly above the dimple. When the dimples are offset from the spray nozzle, areas 16 of the dimple may not be covered by the paint or coating, or may not be covered with a desired thickness of paint or coating, as illustrated schematically by arrows 13b, 13c and dimples 14b, 14c leaving areas 16 uncovered or thinly covered.

In other situations, land area 15 may be thinly covered while the paint or coating may pool inside the dimple. Additionally, the spray nozzle may become partially clogged causing the spray to be asymmetric and create unpainted areas. Hence, it is desirable for an automated inspection system that efficiently identifies unpainted or uncoated areas and alerts responsible people who control the production lines as early as possible.

Infrared imaging (thermography) is a non-contact optical method where an accurate two-dimensional mapping of steady or transient thermal effects is constructed from the measurement of infrared energy emitted by the target. Recent advances in infrared technology, specifically development of high-density imaging sensors have opened a new level of applications unreachable prior to the availability of this technology. Real-time infrared image acquisition and processing allows implementation of advanced thermographic test methods. One of the methods selected for the coating inspection is an active or transient thermography. This method is dissimilar to the conventional thermographic methods in the utilization of time-dependent heating (or cooling) of the target. Depending on the type of defect and thermal characteristics of a target, an external heating or cooling is applied in the form of the short energy pulses. This energy pulses can be generated by using quartz lamps or hot-air heating. Thermal perturbation is then followed by a differential time-resolved infrared image analysis. Coating defects such as blistering and subsurface corrosion spots, can be detected in infrared images as a result of the differences in the thermal diffusivity of the defective and nondefective areas. Often a fraction of a degree is adequate for reliable detection and identification of the thermal signature of the defect. The same technique can potentially be used for rapid assessment of the variations in the coating thickness.

In accordance to one aspect of the present invention, an infrared sensor can detect the unpainted or uncoated areas immediately after the paint or coating is applied to the ball. After the paint or coating is applied, the solvents evaporate from the ball's surface by convection and create a cooling effect on the surface of the ball. This transient cooling causes the temperature on the surface of the ball to drop. The solvents can be chemical solvents or water solvents, and if solvents are utilized, they can make up from 0.5% to about 80% by volume of the coating or paint. When the coating or paint has 0.5% solvent, the surface of the ball would still experience a cooling effect de to the difference in temperature between the ball and the coating. Chemical solvents include oxygenated solvents, including ketones, esters, alcohols and glycol ethers, hydrocarbon solvents, including olefins, porafins, naphthenes and aromatics, chlorinated hydrocarbon solvents, and nitroporafin solvents.

All matters or objects having a temperature above absolute zero (0° K) continuously emit energy to the environment in the form of infrared radiation. This infrared energy has frequency in the electromagnetic radiation spectrum above the visible range and therefore cannot be detected by the human eye. The amount of energy radiated at any given wavelength is dependent on the temperature of the radiating object. The radiated infrared energy is detectable and quantifiable as the radiating object's temperature through an infrared thermography technique.

The infrared portion of the electromagnetic spectrum is in the range of 1-1000 micrometers. Electromagnetic radiation in the form of infrared rays is emitted from the top 1/1000 of an inch of the surface of a radiating object. Infrared thermographic instruments are non-contact, non-intrusive systems that see only radiated energy from the top 1/1000 inch of most objects. In general, thermographic instruments can see the emitted energy from objects that are at a temperature of approximately −35° C. or higher, in the near infrared range of about 0.75 to about 2 micrometers, middle infrared range of about 2 to about 6 micrometers and far infrared range of about 6 to about 14 micrometers and extreme infrared range of about 14 to about 1000 micrometers. These systems are not dependent on reflection of visible light or high temperatures. As long as there are objects above a temperature of −35° C., an infrared thermographic system can see as well in total darkness as it can in full sunlight.

The photonic, infrared energy emitted by objects, is focused by a lens onto a specialized detector. The lenses are preferably made of IR transparent materials, such as germanium, silicon, or zinc selenide, and are not transparent to visible light. The detectors in many systems today are so-called un-cooled thermal detectors made from materials such as vanadium oxide, and barium strontium titanate. Other detector materials such as indium antimonide and indium gallium arsenide are also in use in a variety of infrared thermographic systems. Most of the newer systems on the market today are based on Focal Plane Arrays (FPAs). These systems have higher resolution compared to the old single element infrared cameras, being comprised of 320×240 individual detector elements which produce a display made up of 76,800 picture elements or pixels. The energy that strikes the detector in the camera is converted to an electrical impulse. This electrical impulse then produces a video type image on a CRT or LCD display screen in black and white or a series of selectable color pallets. In general, higher temperature of object or an area in the field of view causes brighter color on the screen. An infrared thermographic image is representative of the thermal patterns in the scene and has no relationship to what our eyes see in the visible electromagnetic radiation. Infrared thermographic cameras cannot see through glass, plexi-glass or other materials that are transparent in the visible wavelengths.

Higher end infrared cameras can also measure this radiated energy and through the use of an onboard computer give calculated temperatures. These temperatures are only valid if the proper parameter values are inputted. This type of thermographic system is called an imaging radiometer or a quantitative infrared system. Infrared thermographic systems that do not calculate temperatures but only display an image are simply called imagers or qualitative devices. Additional information concerning infrared thermography is available at www.infraredthermography.com.

A readily apparent advantage of the present invention is that illumination of the objects to be inspected is no longer necessary, since the IR sensor/camera does not detect illumination. Preferably illumination, if any, is positioned sufficiently away from the objects to be inspected so as not to raise the temperature of these objects.

Unpainted or uncoated balls appear lighter (warmer) and painted balls appear darker (cooler) immediately after painting or coating. Solvent evaporation and/or cooler temperature of the paint or coating temporarily bring down the surface temperature of the balls. Hence, it is preferable that the infrared images of the balls be taken simultaneous with or as soon as practicable after the painting or coating operation to capture this transient effect. Depending on the sensitivity or resolution of the infrared sensor/camera, i.e., the available pixels in the field of view, small unpainted or insufficiently painted areas can be identified.

Figure 2:
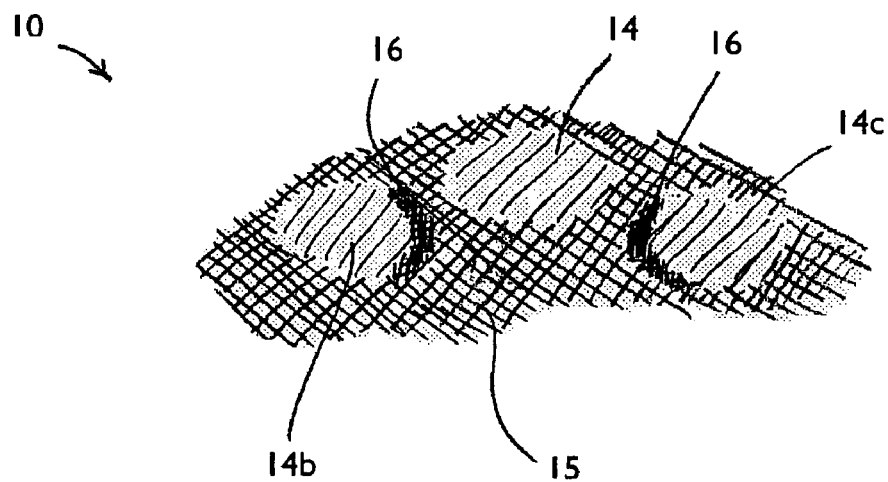
FIG. 2 is a schematic view of an infrared image of the golf ball of FIG. 1.

As shown in FIG. 2, an infrared image is typically grainy, unpainted or insufficiently painted areas 16 appear lighter than the rest of the ball. Land area 15 may appear darker or lighter than dimples 14 depending on whether paint or coating pools in the dimples.

When the ball is properly painted or coated, the variation in color or brightness (if the image is black and white) is relatively low, since evaporation should be fairly uniformed throughout the ball. When the paint or coating is irregular, the variation would be greater. Since the IR image is digitally represented at each pixel, statistical analysis or other numerical analysis can be performed quickly to ascertain whether the ball was properly painted of coated.

In one example, a properly or evenly painted ball can be imaged by the IR sensor/camera to create a calibrated image. Subsequent images of production balls are compared to the calibrated image and the differences in color or brightness can be added up. If the total value of the pixels or the total value of the differences is higher or lower than a total threshold value by a predetermined amount, then the ball can be classified as improperly painted or coated.

In another example, a predetermined individual threshold value for each pixel can be established, e.g., from the calibrated image, and when a predetermined number of pixels has color or brightness value greater than the threshold value, then the ball can be considered as improperly painted or coated. The individual threshold value can be a mean or median value of the pixels.

In another example, the IR image can be manually examined by the operator. The present invention is not limited to any specific method of inspection. Additionally, the background should be subtracted from the image. These IR measurements are non-intrusive, non-invasive and passive.

Suitable IR sensors/cameras include any commercially available devices. Preferably, these devices should have a high number of pixels, e.g., at least 240 pixels, to provide adequate resolution and sufficient temperature sensitivity, e.g., ± about 0.10° C. to about 0.25° C. at room temperature. An acceptable IR sensor/camera is the Thermovision® 570 commercially available from Agema Corp. Other suitable IR sensors/cameras include those available from Nikon (JP), Infrared Systems, Inc. (Reno, Nev.), Electrophysics, Infrared Solutions, Inc. (Plymouth, Minn.), among others.

In accordance with another aspect of the present invention, the golf balls are heated before being painted or coated. Heating prior to painting or coating accelerates the evaporation of solvents. The balls are typically pre-heated from 90° F. to about 150° F. Pre-heating golf balls is discussed in commonly owned, co-pending U.S. app. Publ. No. 2004/0022948, which is incorporated herein by reference in its entirety.

Another inspection step can include inspection of the paint and coating gloss. This is preferably accomplished in the visible region of the electromagnetic radiation spectrum. One such technique is specular gloss measurement using a goniophotometer. Specular gloss measurement is disclosed in "NIST Reference Goniophotometer for Specular Gloss Measurements," by M. Nadal and E. Thompson, Journal of Coatings Technology, Vol. 73, No. 917 (June 2001) and "New Primary Standard for Specular Gloss Measurements," by M. Nadal and E. Thompson, Journal of Coatings Technology, Vol. 72, No. 911 (December 2000). These references are incorporated by reference herein in their entireties.

Gloss is simply the "shininess" of a surface, with a mirror finish at one extreme and a matte velvet at the other. And like color, gloss has a physiological property, in that it depends not only on the physical properties of surfaces, but also on human perception. In appearance measurements, gloss is important as it imparts a perception of quality. ISO 2813 (1994) defines specular gloss as "the ratio of luminous flux reflected from an object in a specular direction for a specified source and receptor angle to the luminous flux reflected from glass with a refractive index of 1.567 in a specular direction". Thus a measure of the glossiness of a surface is the quantity of light reflected from a test surface (at a specified angle), compared with that of a standard surface which is a black glass. The specified angle is that measured from the normal to the test surface. It is important to specify this angle, since the gloss may vary greatly as the viewing angle is changed. For example, a sheet of paper on a desk appears to have a matt finish, but the same sheet of paper looks shiny when held up to the light and viewed from a very low angle (i.e. a>80°). Typical angles are 20°, 45°, 60°, 75° and 85°.

As disclosed in these references, the measurement of specular gloss consists of comparing the luminous reflectance from a test specimen to that of a gloss standard under the same geometric conditions. Generally, the appearance of an object is the result of an interaction of the light incident on the object, the optical characteristics of the object and human perception. The measurements have been standardized by the Commission Internationale de l'Eclairage (CIE). Appearance attributes of an object can be roughly divided into chromatic attributes and geometric attributes. Chromatic attributes vary the spectral distribution of the reflected light (color) and geometric attributes vary the spatial or angular distribution of the reflected light (gloss and haze). Theoretical basis and suitable instrumentations are fully disclosed in the two incorporated references.

As applied to golf ball inspection, a light source is focused on to the surface of a painted or coated ball, and the reflected light or gloss is received by a detector. The reflected light would be different (or lower) from unpainted or uncoated spots than from painted or coated areas. To compensate for the reflection off of dimple surfaces with constantly changing surface contours, the detector can compare the reflected light off a golf ball to be inspected with the reflected light off a calibrated ball, e.g., a properly painted or coated golf ball. Differences between these two reflected lights indicate different gloss attributes or existence of unpainted or uncoated spots.

Another inspection step can include projection and shadow moiré technique. This technique is discussed in "Enhancement of Surface Inspection By Moiré Interferometry Using Flexible Reference Gratings," by J. Matinez-Anton, H. Canabal, J. Quiroga, E. Bemabeu, M. Labajo and V. Testillano, Optic Express, Vol. 8, No. 12 (June 2001), in "Moiré Fringe Contouring," available from www.faraday.gla.ac.un/moire-.htm and in U.S. Pat. No. 4,641,972. These references are incorporated by reference herein in its entirety.

Generally, the projection and shadow moiré technique involves projecting light through a grating onto an object to produce a shadow grating. An image of the object is formed in the plane of a reference grating, which can be observed through the same or different grating. A CCD camera captures this image. The interaction of the superimposed projection grating lines with the reference grating causes moiré fringes to form which appear to be superimposed on the surface of the object being measured. This technique is capable of measuring the contours of an object (e.g., dimples), and should detect defects in the contours caused by uneven painting or coating.

Another inspection step can include laser shearography technique. This technique is discussed in "Laser-Shearography for Nondestructive Testing of Large Area Composite Helicopter Structures," by R. Pezzoni and R. Krupta, (Rome, Italy, 2000) available at www.ndt.net/article/wcndt00/papers/idn732/idn732.htm, and "Emerging NDE Technologies and Challenges at the Beginning of the $3^{rd}$ Millennium, Part I, Part II," by Y. Bar-Cohen, NDT.net, Vol. 5, No. 1 (January 2000). These references are incorporated by reference herein in its entirety.

Generally, laser shearography is a variation of holography. Shearography is an optical video strain gauge. The technique senses out-of-plane surface displacements in response to an applied load. A stress is applied to the object to be inspected to locate strain caused by internal defects. Data is presented in the form of a fringe pattern produced by comparing two states of the test sample, one before and the other after a load is applied. Electronic shearography incorporates a CCD camera and frame grabber for image acquisition at video frame rates. Fringe patterns are produced by real time digital subtraction of the deformed object image from the reference object image. Shearography also uses a 'common-path' optical arrangement, which provides reasonable immunity to environmental disturbances such as room vibrations and thermal air currents. As a result, shearography can be implemented without the need for sophisticated vibration isolation that is required for conventional holography. The capability of Shearography to inspect large areas in real time has significant advantages for many industrial applications including inspection of composite structures and pressure vessels. To stress the test structure, various techniques are used, where the most effective are thermal and surface vacuum techniques. Thermal shearography is used to inspect near surface defects, such as skin-to-core bondline, ramp areas and solid graphite laminates, and vacuum stress shearography is used to examine both near and far side bond lines in the honeycomb areas. Thermal stress shearography has been shown to be capable of inspecting large areas at a rate of 60-$ft^2$/hour. Thermal shearography can be used to defect surface defects such as uneven painting or coating.

Another inspection step can include diffracto-sight, available from Diffracto Ltd. of Canada. Diffracto-sight is an optical double-pass retroreflection surface inspection technique for visualizing very small out-of-plane surface distortions, such as indentations and protrusions, as well as unpainted areas on golf balls.

A diffracto-sight inspection system consists of a CCD camera, a white light source mounted above the camera lens and a retro-reflective screen. A schematic of such as system is disclosed in "Emerging NDE Technologies . . . ," incorporated by reference above. The light reflects off of the object to be inspected and is intercepted by the screen, which is preferably made from reflective micro-bead layer. While the screen reflects most of the light in the same direction of the incident light, a small amount of light is dispersed. When the surface of the object to be inspected is illuminated by the light source, the local curvatures are focusing or dispersing light onto the retro-reflective screen. A light pattern is formed on the screen and is reflected back to the source with a slight dispersion. This path is backlighting the surface of the object to be inspected and enhances the scattering effect of surface deformations. By viewing this surface slightly off-axis from the light source, a unique pattern appears near the local surface deformations. This pattern comprises bright and dark gray scale variations. Unpainted or uncoated areas should have these unique patterns appearing close to them.

While it is apparent that the illustrative embodiments of the invention disclosed herein fulfill the preferred embodiments of the present invention, it is appreciated that numerous modifications and other embodiments may be devised by those skilled in the art. Examples of such modifications include slight variations of the numerical values discussed above. Hence, the numerical values stated above and claimed below specifically include those values and the values that are approximately or nearly close to the stated and claimed values. Therefore, it will be understood that the appended claims are intended to cover all such modifications and embodiments, which would come within the spirit and scope of the present invention.

We claim:

1. A method for coating and inspecting an outer surface of a golf ball comprising a plurality of dimples, comprising the steps of
    (i) spraying the outer surface of a first golf ball with a liquid coating comprised of 0.5% to 80% of solvent;
    (ii) providing at least one sensor capable of obtaining images of the golf ball in the non-visible infrared electromagnetic radiation range;

(iii) obtaining at least one image of the outer surface of the golf ball using said sensor wherein the same wavelength region of the infrared electromagnetic radiation range is used for each image after said liquid coating has been applied to the surface of the golf ball and while said solvent evaporates and creates a cooling effect, each image comprising an array of pixels, each pixel being represented by a numerical value indicative of a color or brightness for the given pixel; and (iv) determining whether the liquid coating was applied evenly on the surface of the outer surface of the golf ball by:
  a) obtaining a calibrated image of a second golf ball having an outer surface that has been evenly coated with the liquid coating using the sensor at the same wavelength region of the infrared electromagnetic radiation range used for each image of the first golf ball;
  b) establishing a total threshold value by adding together the numerical values of the pixels in the calibrated image of the second golf ball; and
  c) adding the numerical values of the pixels in the image of the first golf ball, wherein if the sum of the numerical values of the pixels in the image of the first golf ball is different than the total threshold value by more than a predetermined amount, the liquid coating is determined as being applied unevenly.

2. The method of claim 1, wherein the infrared electromagnetic range is from about 0.75 micrometers to about 2 micrometers.

3. The method of claim 1, wherein the infrared electromagnetic range is from about 2 to about 6 micrometers.

4. The method of claim 1, wherein the infrared electromagnetic range is from about 6 to about 14 micrometers.

5. The method of claim 1, wherein the infrared electromagnetic range is from about 14 to about 1000 micrometers.

6. The method of claim 1, wherein the sensor in step (ii) comprises focal plane arrays.

7. The method of claim 1, wherein in step (iii) the image is obtained in an environment substantially free of visible light.

8. The method of claim 1, wherein in step (iii) the image is obtained in an illuminated environment.

9. The method of claim 1, wherein in step (iii) the image is taken during the transient period from the time when the liquid is first applied to the object to the time when the object obtains thermal equilibrium.

10. The method of claim 1, wherein in step (i) the liquid coating is paint.

11. The method of claim 1, wherein if the sum of the numerical values of the pixels in the image of the first golf ball is more than the threshold value by the predeteunined amount then the liquid was applied unevenly.

12. The method of claim 1, wherein if the sum of the numerical values of the pixels in the image of the first golf ball is less than the threshold value by the predetermined amount then the liquid was applied unevenly.

13. The method of claim 1, wherein the dimpled golf ball is heated to 90° F. to about 150° F. prior to spraying the liquid coating thereon.

\* \* \* \* \*